United States Patent
Smith, Jr. et al.

(10) Patent No.: US 7,287,745 B2
(45) Date of Patent: Oct. 30, 2007

(54) LIQUID-CONTINUOUS COLUMN DISTILLATION

(75) Inventors: Lawrence A. Smith, Jr., Houston, TX (US); Mitchell E. Loescher, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 11/455,341

(22) Filed: Jun. 19, 2006

(65) Prior Publication Data

US 2006/0235092 A1 Oct. 19, 2006

Related U.S. Application Data

(60) Continuation of application No. 11/034,463, filed on Jan. 13, 2005, now Pat. No. 7,091,252, which is a division of application No. 10/357,123, filed on Feb. 3, 2003, now abandoned.

(60) Provisional application No. 60/359,209, filed on Feb. 22, 2002.

(51) Int. Cl.
*B01F 3/04* (2006.01)

(52) U.S. Cl. .................. 261/96; 261/109; 261/121.1; 203/99

(58) Field of Classification Search ............. 261/94, 261/96, 97, 109, 110, 113, 114.1, 121.1, 124, 261/126; 203/99
See application file for complete search history.

(56) References Cited

U.S. PATENT DOCUMENTS

| | | | | |
|---|---|---|---|---|
| 3,432,994 A | * | 3/1969 | Whiton et al. ............... 95/211 |
| 3,681,202 A | | 8/1972 | Funkhouser ................ 203/35 |
| 4,766,155 A | | 8/1988 | Sun et al. |
| 4,780,481 A | | 10/1988 | Courty et al. |
| 4,978,807 A | | 12/1990 | Smith, Jr. .................. 568/697 |
| 5,047,179 A | | 9/1991 | Nye ....................... 261/114.1 |
| 5,073,236 A | | 12/1991 | Gelbein et al. |
| 5,087,780 A | | 2/1992 | Arganbright ................ 585/259 |
| 5,118,873 A | | 6/1992 | Smith, Jr. .................. 568/697 |
| 5,118,896 A | | 6/1992 | Steigelmann et al. ....... 585/467 |
| 5,266,546 A | | 11/1993 | Hearn |
| 5,332,552 A | | 7/1994 | Chang ....................... 422/140 |
| 5,348,982 A | | 9/1994 | Herbolzheimer et al. ... 518/700 |
| 5,431,890 A | | 7/1995 | Crossland et al. |
| 5,543,546 A | * | 8/1996 | Tsuneki et al. ............. 558/270 |
| 5,730,840 A | | 3/1998 | Hampl, Jr. et al. |
| 5,730,843 A | | 3/1998 | Groten et al. |
| 5,827,902 A | | 10/1998 | Maretto et al. ............. 518/706 |
| 5,877,363 A | | 3/1999 | Gildert et al. .............. 585/260 |
| 5,921,109 A | | 7/1999 | Billingham et al. .......... 62/643 |
| 5,922,190 A | | 7/1999 | Guitian et al. ................ 208/46 |
| 5,939,350 A | | 8/1999 | Singleton et al. ........... 502/230 |
| 5,954,924 A | | 9/1999 | Art ............................. 203/1 |
| 5,961,933 A | | 10/1999 | Casanave et al. ........... 422/211 |
| 5,994,567 A | | 11/1999 | Kingsley et al. ............ 552/208 |
| 6,123,323 A | * | 9/2000 | Yoneda et al. ................ 261/96 |
| 6,162,754 A | | 12/2000 | Maretto et al. ............... 502/31 |
| 6,169,218 B1 | | 1/2001 | Hearn et al. ................ 585/260 |
| 6,345,811 B1 | | 2/2002 | Yu et al. ....................... 261/97 |
| 6,440,299 B2 | | 8/2002 | Hearn et al. ................ 208/189 |
| 6,495,732 B1 | | 12/2002 | Hearn et al. ................ 585/664 |
| 2001/0021724 A1 | * | 9/2001 | Arcuri et al. ............... 518/722 |
| 2006/0290016 A1 | * | 12/2006 | Smith et al. ............. 261/114.1 |

OTHER PUBLICATIONS

Warren L. McCabe and Julian C. Smith, Unit Operations of Chemical Engineering, Chapter 21, Gas Absorption, pp. 639-645. 2006.

* cited by examiner

*Primary Examiner*—Scott Bushey
(74) *Attorney, Agent, or Firm*—Osha Liang LLP

(57) ABSTRACT

Bubble columns fractionate with vapor-liquid mass transfer efficiencies approaching that of distillation towers when vapor velocities in excess of 50% of jet flood are used. If the vapor velocities are pushed above about 70% of jet flood then the distillation performance of a given column packing becomes similar for both liquid continuous operation (bubble column mode) and vapor continuous operation (ordinary distillation tower mode).

7 Claims, 4 Drawing Sheets

LIQUID-CONTINUOUS COLUMN DISTILLATION

This is a continuation of application Ser. No. 11/034,463 filed on Jan. 13, 2005, now U.S. Pat. No. 7,091,252, which is a division of 10/357,123 filed on Feb. 3, 2003, now abandoned which claims the benefit of U.S. Provisional application No. 60/359,209, filed Feb. 22, 2002.

BACKGROUND OF THE INVENTION

1. Field of the Invention

The present invention relates to the operation of liquid-continuous distillation columns, in particular bubble columns.

2. Related Information

In its broadest sense a bubble column may be a column of liquid with a stream of gas bubbles passing upward through the liquid. Thus, these systems (excluding the column) are comprised of at least two components, i.e., the liquid and the gas. In these systems, unless it is an esthetic display item such as a lava lamp, there is an interaction between the liquid and the gas. For example, in a fish tank, air bubbling up through a column of water is partially absorbed into the water. In other systems, for example, an impure gaseous mixture may be passed through a liquid wash to remove the impurities or to remove the desirable component into the liquid such as capturing volatile organic compounds (VOC) from air which is washed in countercurrent flow with a suitable VOC solvent.

The present invention is particularly useful to a more specialized form of bubble column wherein there are three phases, the liquid, the gas and solid. Very frequently the solid component is comprised of particles which may be inert or catalytic. The solid component may be internal structures in the column such as heat exchanger tubes, baffles, trays or plates. The column may be relatively open or may be a packed column. The packing may be inert or catalytic. The packing may be fluidized, slurried solids or may contain both slurry and packing structures. Thus, the bubble systems may be used for extraction and/or reaction and extraction.

Extractive distillation may be carried out to fractionate a mixture while a high boiling solvent for a material or impurities is introduced near the top of the column to selectively extract a material or impurity during the distillation. However, there is no liquid level in the column above the kettle, thus vapor continuous and not a bubble column.

Historically bubble columns are operated liquid full with vapor flow rates that promote gross back mixing. Internals are sometimes employed to help promote plug flow of the vapor phase but back mixing of the liquid phase causes conditions where little or no fractionation occurs. The normal recommended vapor velocities are significantly below 50% of the jet flood point. In fact, the term "flood point" is not usually used in bubble column operation and must be defined by ordinary distillation tower operation. A principal industrial use of bubble columns is in the Fischer-Tropsch synthesis.

SUMMARY OF THE INVENTION

Operating conditions have been discovered that will allow bubble columns to fractionate with vapor-liquid mass transfer efficiencies approaching that of distillation towers. It has been found that vapor velocities greater than 50% of jet flood to less than 100% of jet flood will promote fractionation in bubble columns. Preferably, if the vapor velocities are pushed above about 70% of jet flood then the distillation performance of a given column packing becomes similar for both liquid continuous operation (bubble column mode) and vapor continuous operation (ordinary distillation tower mode).

The same tower can be operated either as a bubble column or as a distillation tower simply by controlling the liquid level above the packing or below it (usually in the reboiler for a distillation column) so that the packing is either in a liquid continuous mode or a vapor continuous one. The "flood point" (100% of jet flood) is defined as the point where vapor velocities are so great that reflux cannot return to the reboiler fast enough to maintain reboiler level. Above this point, the reboiler will run dry and no steady state operation can be maintained. A flow map may be used to define the jet flood point over a range of reflux ratios. The column packing or other internals (including trays or heat exchanger bundles) will not significantly alter the performance improvements disclosed here that result from operating at a high vapor rate expressed as a % of jet flood.

DETAILED DESCRIPTION

In carrying the present invention there will usually be three phases, although the solid phase is not required to carry out the liquid filled column distillation at over 50% of jet flood, in most applications there will be a solid phase. Simple distillation structures, such as rings, ball, polylobs, saddles or fibrous type structures, trays bubble, sieve etc.), or other distillation structures as known in the art, including the catalytic distillation structures of the type described in U.S. Pat. Nos. 5,266,546, 5,431,890, 5,073,236, 5,431,890 and 5,730,843 which are incorporated by reference. The solid phase may be particulate material, which can be inert or catalytic, for example as in the Fischer-Tropsch synthesis, which may be fluidized or in a slurry (frequently recycling in the system).

In conducting the present liquid continuous distillation, the liquid may be merely materials to be separated by fractional distillation, or there may be added at the upper end of the column a liquid which is higher boiling, and which is intended to extract one or more components from the vapor in the column and exits as a bottoms. The liquid and vapor in the column may be reactive and the reaction product and feed may be separated more efficiently by the present distillation than by the mere stripping action of the gas at less than 50% of jet flood.

The present distillation is particularly useful to separate mixtures of organic compounds, such as hydrocarbons.

In one embodiment the improvement is used in the production of methanol from synthesis gas (carbon monoxide, carbon dioxide and hydrogen). A by product of the reaction is dimethyl ether (DME). Catalysts which are useful for the reaction CO, $CO_2$ and $H_2$ contain copper and zinc oxides and may contain other modifiers such as those shown in U.S. Pat. Nos. 4,766,155 and 4,780,481. One suitable catalyst is Süd-Chemie (formerly United Catalyst Inc.) C-79 which may be described as comprising copper and zinc on ¼" extrudates. Since it appears that metallic copper is the active catalyst, it is desirable to reduce the catalyst before use. Preferably the molar ratio of Cu/Zn is 1 or greater than 1, e.g., to 10 and the Al content is 10 or less mol. %. Zinc oxide helps in take formation of high copper metal surface area, slows agglomerization of the copper particles, traps Cu poisons and reacts with alumina to inhibit DME formation.

Figure 7:
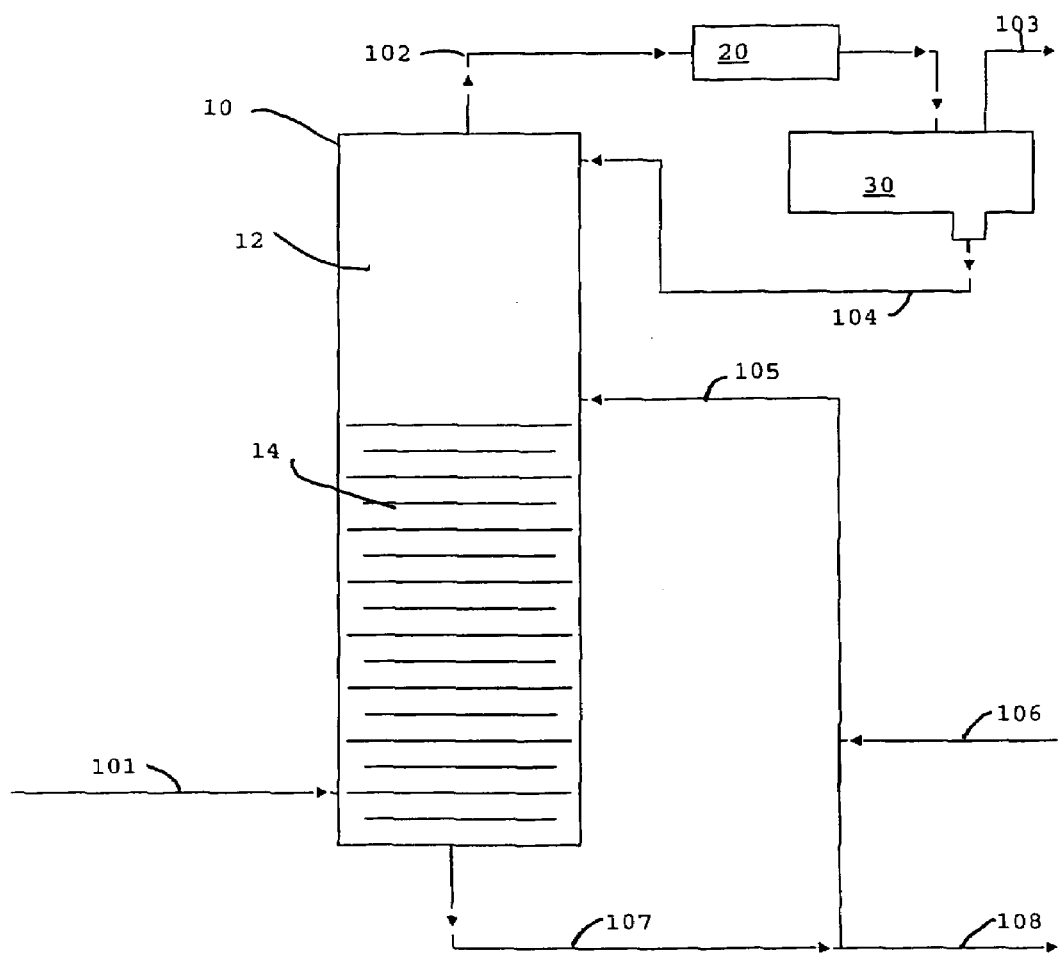
FIG. 7 is a flow diagram of a methanol process utilizing the present invention.

Referring now to FIG. 7, the process for methanol production uses a catalyst slurried in a solvent and fed via flow line 105 into a column 10 having above a zone 14 containing a contact structure such as packing or distillation trays or heat exchange bundles. The synthesis gas is fed via flow line 101 below the contact structure and bubbled up through the catalyst slurry wherein methanol and DME are produced as gaseous product. The gaseous product is separated from the catalyst slurry in disengagement zone 12 and removed as overheads via flow line 102. The solvent is condensed in partial condenser 20 and collected in receiver/separator 30 where the methanol and DME products are removed as vapors via flow line 103. The solvent is recycled to the column 10 as reflux via flow line 104. The solvent and catalyst are removed from the column 10 as bottoms via flow line 107. Spent solvent and catalyst are removed via flow line 108. The remainder of the catalyst and solvent are recycled to the tower via flow line 105 with make up solvent and catalyst being added via flow line 106. A benefit occurs when plug flow reaction results are better than mixing. Operating where plug flow occurs also promotes reaction chemistry.

Temperatures in the range of 350-650° F. are preferred. The solvent is selected so as to boil below the temperature in the reactor at the desired pressure. The higher boiling the solvent the lower the pressure needed for a given temperature.

EXAMPLE

Testing was conducted using a system of n-heptane and cyclohexane at 24 PSIA in a 16.8 inch diameter tower. The FIG.S are graphs of data from various packings. The packings are those described in U.S. Pat. No. 5,730,843 with different particulate loadings. The column packing or other internals (including trays or heat exchanger bundles) will affect the jet flood point but will not significantly alter the performance improvements disclosed here that result from operating at a high vapor rate expressed as a % of jet flood.

Figure 1:
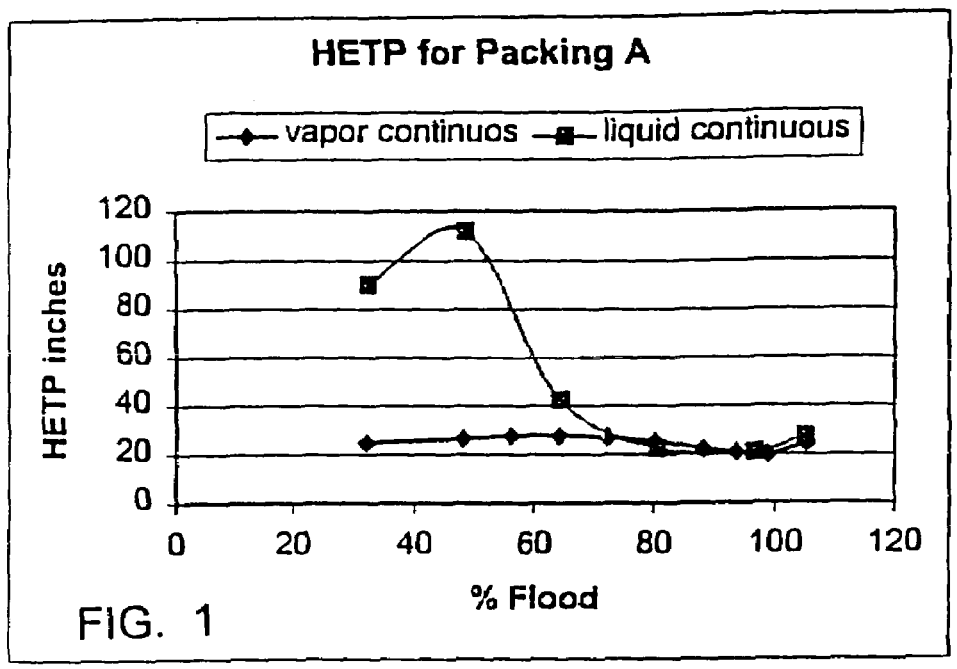
FIG. 1 is a graph showing the HETP for % jet flood for packing A.
Figure 3:
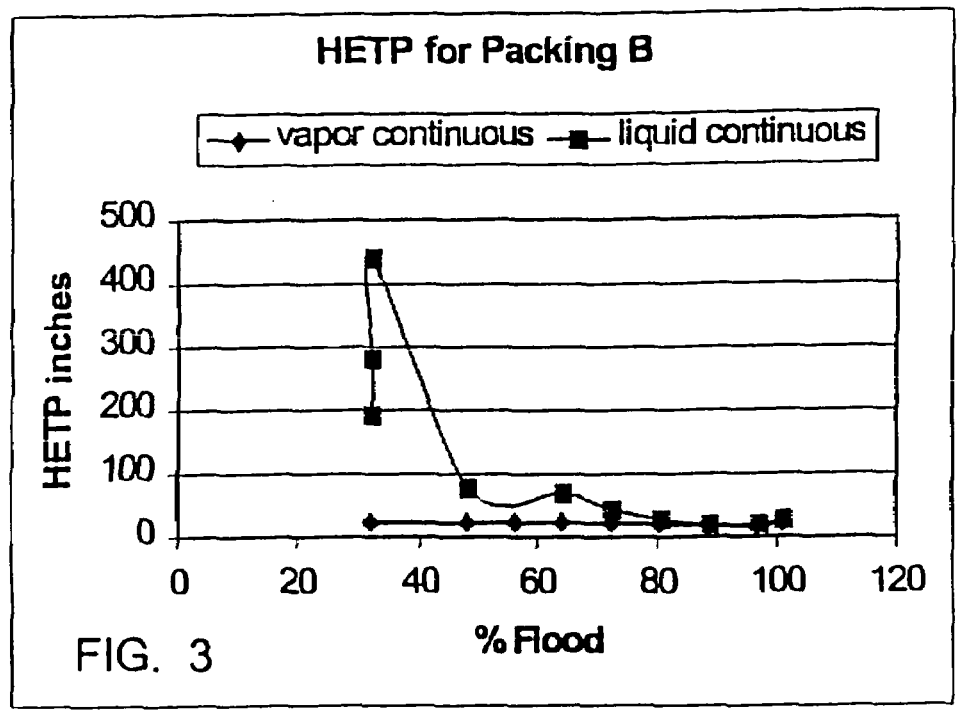
FIG. 3 is a graph showing the HETP for % jet flood for packing B.
Figure 5:
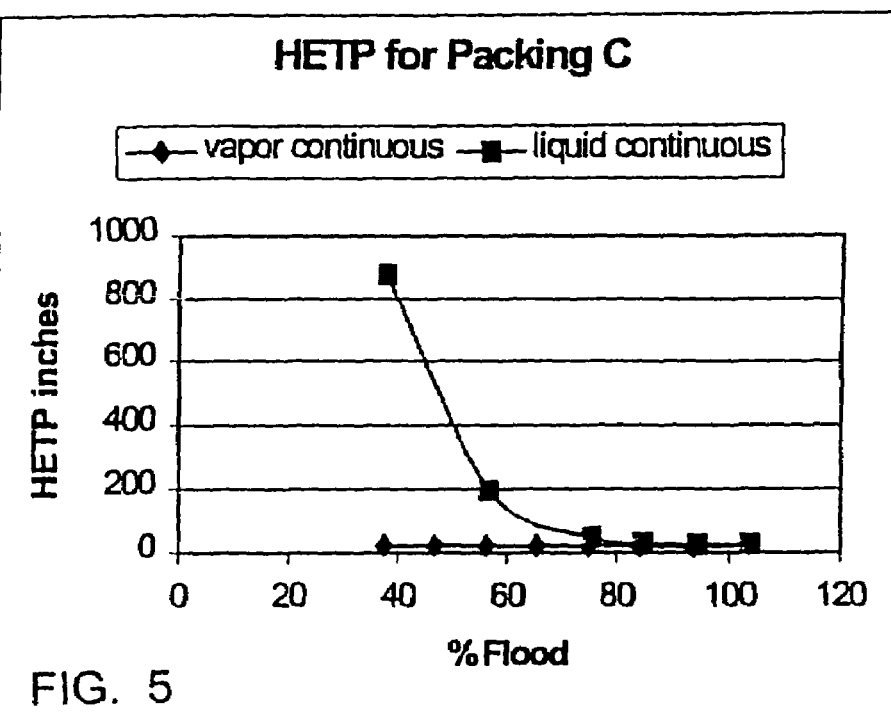
FIG. 5 is a graph showing the HETP for % jet flood for packing C.

As can be seen in each case in FIGS. 1, 3 and 5, the vapor-liquid mass transfer efficiency, as indexed by HETP, improved as the vapor rate increased above about 50% of jet flood. Above about 70% of jet flood the performance was practically the same whether in bubble column mode (liquid continuous) or distillation tower mode (vapor continuous).

Figure 2:
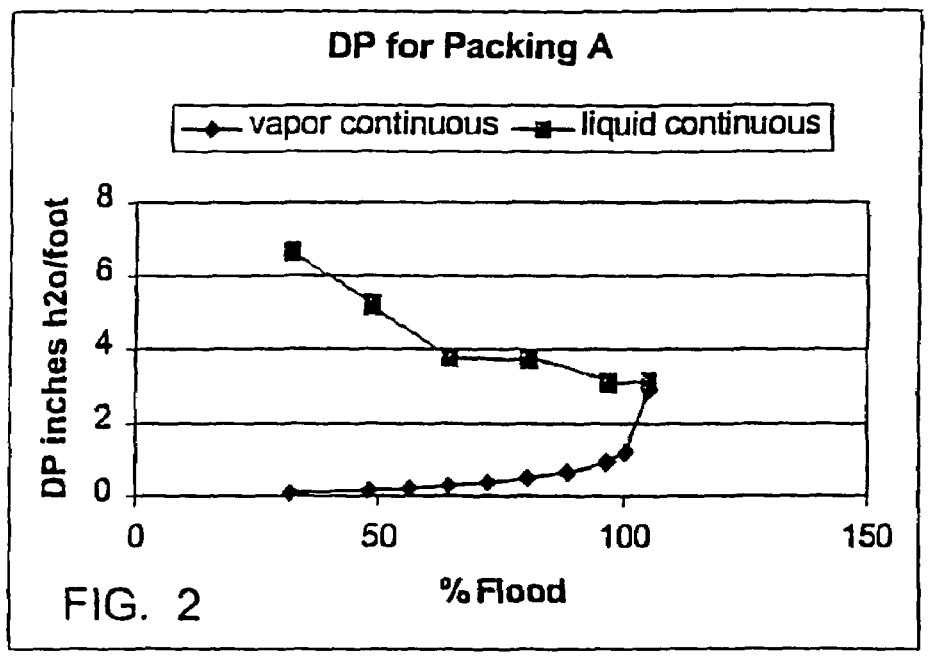
FIG. 2 is a graph showing froth density at % jet flood for packing A.
Figure 4:
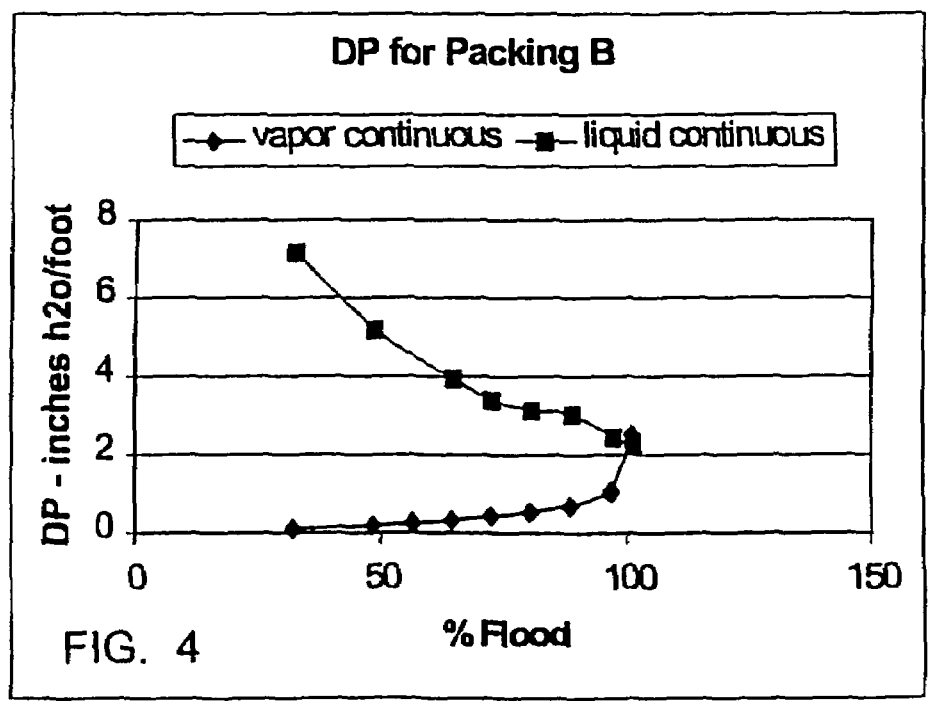
FIG. 4 is a graph showing froth density at % jet flood for packing B.
Figure 6:
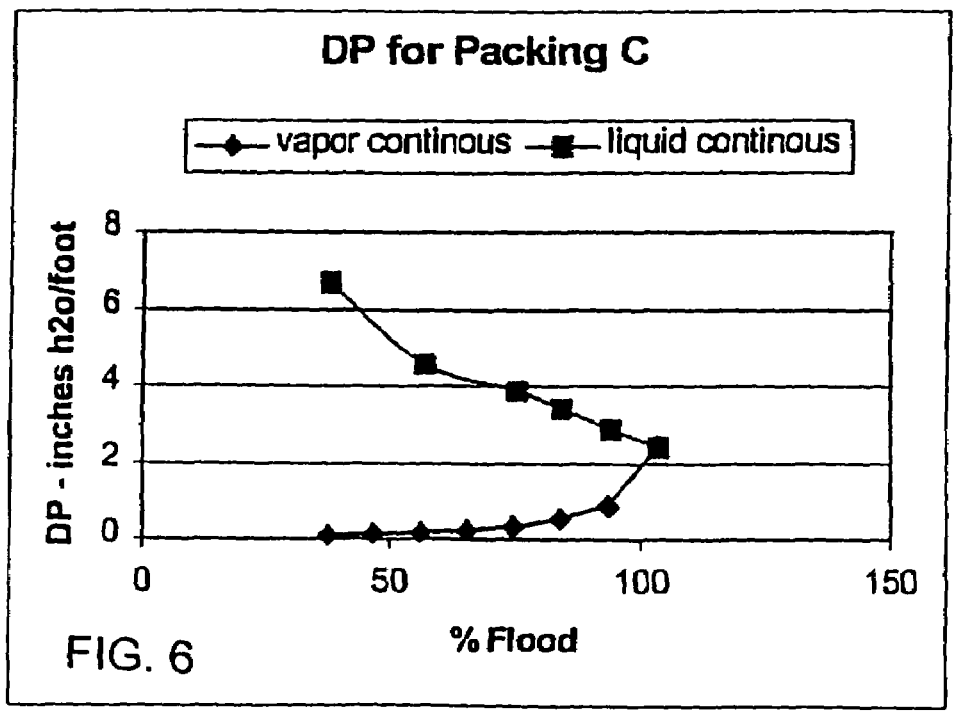
FIG. 6 is a graph showing froth density at % jet flood for packing C.

As the liquid level was raised from the reboiler to the top of the packing there was a seamless, uneventful transition. The system is not full of liquid but is actually full of froth (a mixture of vapor and liquid). The presence of vapor provides a great deal of compressibility to dampen any sudden movements. The froth density can be seen from the above FIGS. 2, 4 and 6 showing DP.

The normal bubble column operation would generally be at less than 30% of jet flood. From the above HETP performance, the initial observation as vapor rates were increased, but still below 50%, was that HETP performance was getting worse. It was surprising that above 50% of jet flood the HETP performance reversed direction and sharply improved. It was even more a surprise that an operating region (above about 70% of jet flood) existed where HETP performance in both liquid and vapor continuous operation closely overlapped.

The invention claimed is:

1. A method of operating a liquid continuous distillation column comprising:
    (a) feeding a first liquid component to said column to essentially fill said liquid continuous distillation column;
    (b) feeding a gaseous component near the bottom of the column at a rate such that the velocity of the gas rising in the column is between 70% and 100% of jet flood to fractionally distill the first liquid component;
    (c) removing a vapor from near the top of the liquid continuous distillation column; and
    (d) removing a liquid from near the bottom of the liquid continuous distillation column.

2. The method according to claim 1 wherein the gaseous component is produced by boiling a second liquid component in a reboiler which is connected to said liquid continuous distillation column.

3. The method according to claim 1 wherein said first liquid is fed near the top of said liquid continuous distillation column.

4. The method according to claim 2 wherein said first liquid is fed near the middle of said liquid continuous distillation column.

5. The method according to claim 1 wherein said liquid continuous distillation column is packed with solid packing and said column is filled to a point above said packing.

6. The method according to claim 1 wherein said first liquid comprises organic compounds.

7. The method according to claim 1 wherein said first liquid comprises hydrocarbons.

* * * * *